US008088408B2

(12) United States Patent
Cravens

(10) Patent No.: US 8,088,408 B2
(45) **Date of Patent: *Jan. 3, 2012**

(54) METHOD AND COMPOSITION FOR DELIVERY OF MEDICANTS TO ANIMALS

(75) Inventor: Ronald L. Cravens, Leawood, KS (US)

(73) Assignee: Astech International LLC, Centennial, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/041,619

(22) Filed: Mar. 7, 2011

(65) Prior Publication Data

US 2011/0165091 A1 Jul. 7, 2011

Related U.S. Application Data

(63) Continuation of application No. 10/084,592, filed on Feb. 25, 2002, now Pat. No. 7,923,023.

(51) Int. Cl.

| | |
|---|---|
| ***A61K 49/00*** | (2006.01) |
| ***A61K 39/00*** | (2006.01) |
| ***A61K 9/00*** | (2006.01) |
| ***A61K 9/70*** | (2006.01) |
| ***A61F 13/00*** | (2006.01) |
| ***A23K 1/18*** | (2006.01) |

(52) U.S. Cl. ........ 424/434; 424/400; 424/438; 424/443; 424/10.1; 424/10.3; 424/184.1; 119/600; 119/602; 119/603; 119/604

(58) Field of Classification Search ........................ None
See application file for complete search history.

(56) References Cited

U.S. PATENT DOCUMENTS

| | | | |
|---|---|---|---|
| 4,402,941 | A | 9/1983 | Vaillancourt |
| 4,692,412 | A | 9/1987 | Livingston et al. |
| 5,122,377 | A | 6/1992 | Miller et al. |
| 5,602,107 | A | 2/1997 | Choi |
| 5,753,244 | A | 5/1998 | Reynolds et al. |
| 5,846,830 | A | 12/1998 | Demello et al. |
| 5,856,364 | A | 1/1999 | Martin |
| 5,906,826 | A | 5/1999 | Emery et al. |
| 6,177,082 | B1 | 1/2001 | Dowling et al. |
| 6,251,405 | B1 | 6/2001 | Becker et al. |
| 6,350,784 | B1 | 2/2002 | Squires |
| 6,410,062 | B1 | 6/2002 | Callaghan et al. |
| 6,541,001 | B1 | 4/2003 | Gallili et al. |
| 7,923,023 | B2 | 4/2011 | Cravens |
| 2002/0025325 | A1 | 2/2002 | Chu et al. |

OTHER PUBLICATIONS

The Merck Veterinary Manual, 8th Edition, 1998, Merck & Co., Whitehouse Station, NJ, USA pp. 348-349, 358-361, 1644-1651, 1866-1869, 1972-1874.
8 in 1 Kittymalt Hairball Remedy Original Malt Flavor, 1999-2008, PetFoodDirect.com. Retrieved online Nov. 26, 2008 (http://www.petfooddirect.com/store/product_detail.asp?pf_ip=3137501&dept_id=113&brand_id=153&Page=).
Madey, Judith. The Other End of the Cow. (In context #16.fall, 2006, pp. 13-17; 2006). Retrieved online on Jul. 27, 2010 at http://www.natureinstitute.org/pub/ic/ic16/cow.htm.
The Straight Dope: why are dogs' noses always wet? (2001-retrieved on Jul. 30, 2010 from http://www.straightdope.com/columns/read/1455/why-are-dogs-noses-always-wet).
Frandson et al, Anatomy and Physiology of Farm Animals, 2009, Chapter 19p. 317, p. 344.
Metzler, S.J. et al, The Nose-Licking Reflex and Its Inhibition, The American Journal of Physiology, vol. 50, No. 3 pp. 377-382, 1919.
Cat Facts, www.siliconhell.com.
Laffont et al., A pharmacokinetic model to document the actual disposition of topical ivermectin in cattle, Vet. Res., 2003, pp. 445-460, vol. 34.
Hoekstra, et al., Further Studies on the Production of a Hyperkeratosis in Calves with Topically Applied Base-Oils for Use in Livestock Sprays, Journal of Dairy Science, 1955, pp. 186-196, vol. 38, Issue 2.
Laffont et al., Licking behaviour and environmental contamination arising from pour-on ivermectin for cattle, Int J Parasitol, Dec. 2001, pp. 1687-1692, Issue 31, vol. 14.
Ahmed et al, Pharmaceutical challenges in veterinary product develop, Advanced Drug Delivery Reviews, Oct. 4, 2002, pp. 871-882, vol. 54, Issue 6, Elsevier Science B.V.
Hasker et al, The use of licking behaviour of cattle to administer medicaments, Australian Journal of Experimenal Agriculture, 1989, pp. 765-769, vol. 29.

*Primary Examiner* — Oluwatosin Ogunbiyi
(74) *Attorney, Agent, or Firm* — Hush Blackwell

(57) ABSTRACT

According to the present invention, a vaccine or pharmaceutical-containing composition is applied to the muzzle area of the animal, which will then naturally use its tongue to clean itself. This behavior will cause the animal to deposit applied composition to the mucosa of the nasal and oral cavities, thus meeting the need for a simple, effective, and efficient vaccination or treatment method.

13 Claims, No Drawings

METHOD AND COMPOSITION FOR DELIVERY OF MEDICANTS TO ANIMALS

RELATED APPLICATION

This application is a continuation of application Ser. No. 10/084,592 filed Feb. 25, 2002, which application issued on Apr. 12, 2011 as U.S. Pat. No. 7,923,023, the entire disclosure of which is incorporated herein by reference.

BACKGROUND OF THE INVENTION

One of the most common diseases in newly received stocker and feedlot cattle is the Bovine Respiratory Disease (BRD) complex. BRD accounts for approximately 75% of morbidity and over 50% of mortality in feedlots (Edwards, A. 1996. Bovine Pract. 30:5). Studies have indicated that BRD manifests its economic losses cumulatively—through the cost of treatment, the cost of lost production and/or salvage, and the cost of death loss (Perino, L. J. 1992. Compend. Cont. Educ. Pract. Vet. 14 (Suppl.):3) These losses make BRD one of the most costly diseases affecting feedlot cattle. Respiratory tract lesions at slaughter correlate with feedlot and carcass performance (Gardner, B. A. et al. 1999. J. Anim. Sci. 77:3168).

In a recent study of the affects of BRD, heifers treated during the study period had lower average daily gain during the period. Heifers treated for BRD had lower marbling scores resulting in a 37.9% reduction in the percentage of carcasses grading U.S.D.A. Choice, or above. Heifers never treated produced a net return (carcass basis) that was $11.48/head more than heifers treated once for BRD, and $37.34/head more than those treated two or more times. (Stovall, T. C., et al. Impact of Bovine Respiratory Disease During the Receiving Period on Feedlot Performance and Carcass Traits, Animal Science Research Report. Oklahoma Agricultural Experiment Station, Oklahoma State University, Stillwater, Okla., USA, 2000.)

Other diseases are of equal or greater economic importance to the cattle industry, which has historically sought to protect livestock from disease, both for economic and public confidence reasons. Immunization of cattle as a means of preventing disease is a common and long-standing practice dating back to Jenner and Pasteur. Immunization is the practice wherein pathogenic biological agents (viruses, bacteria, fungus, rickettsia, protozoa, mycoplasma) have been inactivated, attenuated administered with or without immuno-modulating agents (adjuvants) to animals with the intent of stimulating the animal's immune system such that subsequent exposure to the immunizing or natural agent yields a rapid and specific protective response, thereby avoiding or reducing the severity of disease.

The common means by which commercial vaccines have been administered to animals involves injecting (by use of hypodermic needles) the vaccine material in the skin (intradermal "ID"), in the muscle (intramuscular "IM"), in the subcutaneous tissue ("SC" or "sub-Q")) or applying the product to readily available mucus membranes (in the eye (intraocular "IO"), in the oral cavity (peros "PO"), or in the nasal cavity (intranasal "IN")). Although the poultry industry has used aerosols and water as means of vaccine delivery to large numbers of birds, and the swine industry has used water as a delivery method, there are no aerosol, water or feed vaccines approved for commercial use in cattle, dogs, cats or horses.

In the case of injected products (pharmaceutical or biological), a number of concerns arise. With respect to food safety and consumer concern about meat quality, introduction of material into the animal via injection carries with it the potential of altering the edible product by scaring, staining, infection or adulteration due to components of the product and/or by carrying foreign material into the body as a result of the injection process as well as the potential for needles being left in the animal. The National Cattlemen's Beef Association has identified losses associated with injection site reactions resulting in damage to the animal, meat, hides and undermining consumer confidence in the safety and quality of beef. Additionally, injection requires close physical contact between the animal and the person administering the vaccine. This close physical contact entails risk of injury to both the animal and the person. There is a potential for accidental injection of workers or non-target animals. Proper disposal of used needles is an ongoing concern. With respect to application of the vaccine, it is difficult to assure or identify proper deposition of the dose volume into the approved target tissue, particularly under modern management practices where large numbers of animals are rapidly processed. Injection of companion animals (dog, cat, horse) has animal welfare and owner acceptability concerns as well as the potential for infection, pain and tissue damage at the site of administration, Administration via mucus membranes has several advantages over injected vaccines. Entry of foreign material into edible tissues is avoided. Some pharmaceutical products (insulin—West Pharmaceuticals) have been shown to perform better when applied to mucus membranes as compared to IM or SC injection. The natural route of exposure to the common respiratory and enteric pathogens is via the oral and or nasal route. Stimulation of a mucosally active immune response is better able to prevent or minimize colonization (a prerequisite to infection and disease) by invading pathogens.

Additionally, intranasal administration of vaccines typically stimulates a rapid response and has been shown to be effective in the presence of maternal antibody. There are, however, drawbacks to commercially available cattle vaccines. Products approved for intranasal administration require direct deposition of the vaccine into the nasal cavity (one or both naries). This is stressful to the animal and requires restraint and close physical contact between the animal and person administering the vaccine. In addition, the animal's immediate response is to resist head restraint and attempt to dispel the injected material from the nasal cavity during or immediately following vaccine administration, sometimes into the operator's face, with resulting safety and efficacy concerns.

Water and feed have been used experimentally as a means of vaccine delivery to cattle, however, there are concerns relating to proper dose intake of individual animals. There are no commercial cattle vaccines currently approved for use via feed or water.

Mucosal administration of vaccines has been shown to provide a broad based immune response. This involves both a local and systemic response. Traditionally, vaccines used for mucosal administration have been live or attenuated; as killed antigens tended to be minimally effective when given IN or PO. While live or attenuated vaccines provide a rapid response, the duration of immunity has typically been less than with IM administered products. With the advancement in adjuvant technology and vaccine formulation, it is now possible to increase the duration of immunity as well as allow use of inactivated antigens via the mucosal route. Advancement in formulation of pharmaceutical preparations has also led to development efforts for orally and/or nasally administered products (West Pharmaceutical).

Despite the advances in intranasal and other mucosal administrations of vaccination and therapeutic materials, there remain many needs in the development of safe, effective, and efficient methods of administration of such materials to animals. In particular, the following needs remain unmet by the methods of the prior art:

1. The need to avoid use of needles which may (a) cause damage to edible tissues and hides, (b) incite consumer concern over pet and livestock animal welfare, (c) incite consumer and food industry concern over food safety, (d) raise concerns related to worker safety, and (e) give rise to issues concerning disposal of contaminated medical waste.

2. The need and desire to administer the vaccine to mucosal membranes which is the natural route of infection.

3. The need to avoid (or minimize) close physical contact between the worker and animal in order to reduce the risk of injuries to both.

4. The need to have a visual indicator of vaccination in order to increase compliance and proper administration of vaccine, and to reduce inadvertent multiple vaccination.

BRIEF DESCRIPTION OF THE INVENTION

According to the present invention, a vaccine/pharmaceutical-containing composition is applied to the muzzle of the animal, which will then naturally use its tongue to clean itself. This behavior will cause the animal to deposit a therapeutically effective amount of the applied composition to the mucosa of the nasal and oral cavities, thus meeting the need for a simple, effective, and efficient vaccination/treatment method of administration.

DETAILED DESCRIPTION OF THE INVENTION

The present invention comprises a method for immunizing and/or treating cattle or other animals via application of an approved dose of biological vaccines (antigens) or pharmaceuticals to the muzzle and/or nares area of cattle or other animals via direct application such as a liquid or emulsion paint, spray, paste, mist, roll-on or bio-film. The muzzle of an animal is defined as the facial portion of the respiratory system and rostral portion of the upper and lower jaws collectively, to include the nasal plane, nostrils, medial, lateral, dorsal and ventral borders of the nostrils, the philtrum, superior and inferior lips (labia oris) and the angle of the mouth (angulus oris). This method of application takes advantage of the normal behavior of cattle and other animals to clean their muzzle with their tongue and thereby deposit the vaccine or pharmaceutical material to the nasal and/or oral mucosa. The method thus minimizes the need for physical contact between the human operator and animal, and eliminates the use of needles. The delivery composition of the present invention may contain any formulation comprised of mucosally active antigens and/or biologically active proteins and/or biologically active chemicals (pharmaceuticals) and/or biologically active carbohydrates with or without adjuvants, with or without adherent/viscous components, with or without aromatic and palatable components and with or without a visual or non-visible indicator of application.

Method of Administration

The composition described above may be applied to the muzzle of the animal in any of a variety of methods according to the present invention. For example, the composition may have a viscosity and concentration appropriate for application by brush or roller. It may be applied by liquid spray, with or without atomization. It may be manually applied as a paste, salve, or film. It may be carried on a carrier web such as a tape, adhesive strip, or patch. In short, any method of contacting the animal's muzzle and transferring to it an effective dose of the composition may be employed.

Formulation

The formulation of the compound of the present invention includes, but is not limited to various combinations of the following components for use in all animal species, including cattle, sheep, pigs, cats, dogs, horses, deer, buffalo and other wildlife:

1. Adjuvants or other immune stimulating compounds, such as that described in U.S. Pat. No. 6,262,029 "Chemically Modified Saponins and the Use Thereof as Adjuvants", Aluminum hydroxide salts, Aluminum hydroxide gels, Alum, "Superantigens" which are molecules that stimulate, independent of antigen, those T-cells displaying a particular beta chain variable region (Vbeta) of the T-cell receptor. These molecules are the most powerful T-cell mitogens known, inducing biological effects at femtomolar concentrations. The best characterized superantigens are the microbial toxins from *Staphylococcus aureus* and *Streptococcus pyogenes*.

Other adjuvants useful for the present invention include natural and synthetic immuno-modulating agents, other saponin and saponin derivatives, mycobacterial cell wall extract—Immnoboost® Bioniche Life Sciences Inc., oil emulsions (water in oil or oil in water) such as Amphigen® from Pfizer, Inc., oils (mineral oil, animal derived oils, plant derived oils such as carbopal), or other proprietary and non-proprietary immuno-modulating agents.

2. Palatability enhancers, intended to be attractive to the animal's senses of smell and taste, such as plant-derived flavoring agents including but not limited to molasses, sucrose, fructose and anise.

Biological Antigens/Vaccines

Vaccines are used to prevent and/or treat a multitude of diseases in cattle and other animals. These include diseases of, but are not limited to, the respiratory system, the reproductive system, the urinary system, the gastrointestinal/digestive system, the integument/musculoskeletal system, the hemolymphatic system, the endocrine system, the nervous system, and disease of the eye and ear (Current Veterinary Therapy—Food Animal Practice, Howard, 1981, W. B. Saunders Co.). Organisms included are, but are not limited to, viruses, mycoplasma, chlamydia, protozoa, rickettsia, coccidia, bacteria, fungus (Current Veterinary Therapy—Food Animal Practice, Howard, 1981, W. B. Saunders Co.) and internal and external parasites including, but not limited to, helminths and arthropod parasites as identified in Principle Parasites of Domestic Animals in the United States, Ivens, et. al. 1978, University of Illinois, pp. 30-71. All current licensed products for cattle or other animals are administered via injection, via direct deposit in the nasal cavity, via direct deposit in the oral cavity, in water or in feed, topically applied, or by aerosol. The products are composed of from one to many antigens from a multitude of pathogenic and non-pathogenic biological organisms. The specific formulation may be composed of live, attenuated, killed or altered individual biological organisms acting as the immunizing antigen directly or serving as vectors to deliver the antigen of interest. The biologically relevant protective portion of the organism, be they recombinant or natural, can be present as the whole organism, specific and non-specific subunits of the organisms structural and non-structural components including cell wall, cell wall components, endotoxins, exotoxins (e.g. leukotoxin from *M. haemolytica*), culture media supernatant, intracellular proteins and organelles including nuclear (including DNA/cDNA) and non nuclear elements (including RNA/cRNA). All and/or part of the fore going elements and organisms can be combined with or without immuno-modulating substances (adjuvants) to produce a vaccine designed to prevent and/or treat from one to many diseases following single and/or multiple administrations.

Currently Licensed Veterinary Products may be referenced in the Compendium of Veterinary Products (CVP); Fifth Edition, January 1999; Distributed by North American Compendium, Inc. 942 Military Street, Port Huron, Mich. 48060

The CVP provides a list of all current Federally (USDA/APHIS, FDA, EPA) approved products for use in cattle or other animals in the United States. This list includes brand names, antigens included, formulations, specific claims, and manufacturer for each product. In addition to those listed, there are non-USDA/APHIS approved or products with USDA/APHIS conditional approvals sold in the United States. These include, but are not limited to, vaccines classified as autogenous vaccines which are compounded for individual customers with organisms originating from the particular customers operation (provided by companies including ImmTech, Grand Laboratories, Texas Vet Labs, American Animal Health, individual practicing veterinarians, Universities and others) conditional licenses are granted for disease such as mycoplasmosis (Texas Vet Labs) where no Federally approved vaccine has been developed. In addition, there are new vaccines, and new claims for existing vaccines under development by many companies that can potentially be administered to cattle and other animals via the mucosal surfaces of the nasal and oral cavities. Outside the United States, similar products, antigens, antigen combinations composed and formulated in a manner similar to those produced and/or sold in the United States are common. All known biological agents can potentially be formulated (as the natural agent, or as a component of the organism via traditional and/or recombinant technology and/or as vectors) into a vaccine such that an immune response will be engendered in an animal when administered to the nasal and/or oral mucosa. The scope of this invention is intended to encompass all such current or future developed products or technologies, when the administration method involves application to the external structure of a bovine (or other animal's) muzzle and/or nares without the specific requirement of deposition onto or into the internal nasal and/or oral cavity.

Viscosity

The consistency of the product should be such that it remains in place long enough to allow proper dosage. Mediators of viscosity may be included into the compound formulation to ensure this goal is met.

Aroma

Ingredients may be used to enhance the aroma so as to contribute to palatability, or not detract from animal acceptance and natural behavior.

Identifier

In order to provide post-dosing identification of dose animals, a Light visible (e.g. orange, yellow) or UV or other nonvisible dye may be included in the compound formulation. In this manner, dosed animals may be easily recognized and one may avoid re-dosing them, ensuring proper dosage and saving on materials and labor.

Stabilizers

Appropriate product stabilizers such as to allow for antigen integrity and presentation may be included in the compound formulation.

Preservatives

The compound formulation may contain appropriate preservative ingredients such as antibiotics (e.g. gentamicin, amphotericin B, penicillin, polymyxin B or others), antibacterials or antifungal agents, (e.g. thimerosal, formaldehyde) as deemed appropriate or necessary by APHIS or other relevant regulatory authorities.

Sustained Release Substances

To promote release of active components over a longer time period, ingredients may be included such as inert or biologically active substances so as to extend the time of presentation of the antigen/chemical to the animal's immune system.

Adhesive Components

The compound formulation may contain appropriate component(s), which create additional adhesive capability of the product to adhere to the external nasal mucosa and to the internal oral and nasal tracts. These may include a bio-adhesive type of material that extends the time drug/antigen is available on the nasal or oral mucosa.

While the invention has been described in its preferred embodiments, it is to be understood that the words which have been used are words of description rather than of limitation and that changes may be made within the purview of the appended claims without departing from the true scope and spirit of the invention in its broader aspects. The inventors further require that the scope accorded their claims be in accordance with the broadest possible construction available under the law as it exists on the date of filing hereof, and that no narrowing of the scope of the appended claims be allowed due to subsequent changes in the law, as such a narrowing would constitute an ex post facto law, and a taking without due process or just compensation.

The invention claimed is:

1. A method for treating a bovine animal to achieve a positive effect on the health of the bovine animal comprising:

applying at least a single effective dose of a prophylactic composition directly to the nasal plane of the bovine animal, wherein the bovine animal distributes the single effective dose into its oral and/or nasal cavities to contact the oral and/or nasal mucosa when the bovine animal cleans the nasal plane with its tongue, wherein the prophylactic composition includes at least one prophylactic agent.

2. The method of claim 1 wherein the prophylactic agent further comprises at least one preservative ingredient selected from the group consisting of antibiotics, antibacterials, and antifungal agents.

3. The method of claim 1 wherein the prophylactic composition further comprises at least one performance enhancing component selected from the group consisting of viscosity enhancers, aroma enhancers, sustained release agents, and adhesive enhancers.

4. The method of claim 1 wherein said single effective dose is applied with a brush, roller or as a liquid spray.

5. The method of claim 1 wherein said prophylactic composition is selected from the group consisting of pastes, salves and films.

6. The method of claim 1 wherein said single effective dose is applied via a carrier web.

7. The method of claim 1 wherein said prophylactic agent is a vaccine.

8. The method of claim 1 wherein said prophylactic agent is a pharmaceutical.

9. A method for immunizing a bovine animal comprising:

applying at least a single effective dose of an immunizing composition directly to the nasal plane of said bovine animal, wherein said bovine animal distributes said single effective dose into its oral and/or nasal cavities to contact the oral and/or nasal mucosa when said bovine animal cleans said nasal plane with its tongue, wherein said immunizing composition includes at least one biological agent.

10. The method of claim 9 wherein said biological agent is a vaccine.

11. The method of claim 9 wherein said single effective dose is applied with a brush, roller or as a liquid spray.

12. The method of claim 9 wherein said immunizing composition is selected from the group consisting of pastes, salves, and films.

13. The method of claim 9 wherein said single effective dose is applied via a carrier web.

* * * * *